United States Patent [19]
Ohmi et al.

[11] Patent Number: 5,481,923
[45] Date of Patent: Jan. 9, 1996

[54] HOLDER OF FATIGUE TEST PIECE

[75] Inventors: Masao Ohmi; Fumiki Takada; Minoru Kizaki, all of Ibaraki, Japan

[73] Assignee: Japan Atomic Energy Research Institute, Tokyo, Japan

[21] Appl. No.: 371,445

[22] Filed: Jan. 11, 1995

Related U.S. Application Data

[63] Continuation of Ser. No. 145,567, Nov. 4, 1993, abandoned.

[30] Foreign Application Priority Data

Nov. 6, 1992 [JP] Japan ................... 4-296764

[51] Int. Cl.⁶ .................. G01N 3/08; G01N 3/02
[52] U.S. Cl. .................. 73/860; 73/856; 73/833
[58] Field of Search .................. 73/856, 857, 858, 73/859, 860, 866, 833, 12.07, 12.09, 12.12, 819

[56] References Cited

U.S. PATENT DOCUMENTS

| | | | |
|---|---|---|---|
| 308,957 | 12/1884 | Emery | 73/859 |
| 3,320,798 | 5/1967 | Gram | 73/857 |
| 3,541,838 | 11/1970 | Antonevich | 73/12.09 |
| 3,750,457 | 8/1973 | Pascquet | 73/12.07 |
| 3,908,449 | 9/1975 | Zuber | 73/857 |
| 4,149,407 | 4/1979 | Strom et al. | 73/815 |
| 4,502,338 | 3/1985 | Smith et al. | 73/819 |
| 4,599,891 | 7/1986 | Brauer et al. | 73/819 |
| 4,721,000 | 1/1988 | Scanlon | 73/857 |
| 4,885,941 | 12/1989 | Vardoulakis et al. | 73/819 |

FOREIGN PATENT DOCUMENTS 56-47732  4/1981  Japan ................... 73/857

*Primary Examiner*—Richard Chilcot
*Assistant Examiner*—George Dombroske
*Attorney, Agent, or Firm*—Banner & Allegretti, Ltd.

[57] ABSTRACT

The improved sample holder comprises a cylinder portion 5 having a center hole through which a test piece is inserted, a reciprocating ram rod 7 that is inserted into said hole and which is vertically slidable under hydraulic pressure to push down the test piece, and a test piece fixing plate 6 that is inserted under the cylinder portion 5 as it is slid horizontally from either right or left, with the thicker part of the test piece being held between the fixing plate 6 and the working end of the hydraulically operated pushing rod 7. The holder permits a fatigue test piece to be mounted and fixed on a testing machine by remote manipulation so that a fatigue test can be performed in either a hot vacuum or inert gas atmosphere.

6 Claims, 2 Drawing Sheets

HOLDER OF FATIGUE TEST PIECE

This application is a continuation of application Ser. No. 08/145,567, filed Nov. 4, 1993, now abandoned.

BACKGROUND OF THE INVENTION

This invention relates to a holder of a test piece that is mounted on a fatigue tester for performing a fatigue test on the constituent material of said test piece by applying cycles of tensile and compressive loads to the piece as it is placed in a hot vacuum, or an inert gas atmosphere.

To collect data on the endurance characteristics of metallic and other materials, the fatigue life of those materials is measured with cyclic loads being applied to the test piece as it is mounted on a fatigue tester.

The measurement of fatigue life has conventionally involved the use of a sample holder having the construction shown in FIG. 1; the thicker portion of a test piece indicated by 1 is retained by a fixing adapter 2, which is fitted in a groove cut in a fixing plate 3 in such a way that the distal end of the test piece is inserted through a center hole in the plate 3. The test piece fixing plate 3 carrying the test piece 1 and the adapter 2 is secured to the fatigue tester by manually tightening screws 4.

When performing the fatigue test, the test piece mounted on the fatigue tester is provided with cycles of tensile and compressive loads and hence it has been necessary to securely fix the test piece in position by means of a sample holder.

Particularly in the case where it is exposed to neutron radiations in nuclear reactors and other radioactive environments, the test piece becomes radioactive and to protect the worker from the emitted radiations, tile operations of mounting and dismounting the test piece have had to be done remotely (by use of manipulators).

Fatigue tests recently require prolonged exposure times; in addition, they are conducted at elevated temperatures and this increases the likelihood that corrosion will occur in the test piece. To avoid these problems, it has recently become desirable to conduct a fatigue test either in vacuo or in an inert gas atmosphere.

In this case, too, the fatigue test must be conducted with a plurality of test pieces being replaced as required without destroying the vacuum or inert atmosphere; a need has, therefore, arisen to perform remote manipulation in connection with the mounting or dismounting of the test piece.

SUMMARY OF THE INVENTION

The present invention has been accomplished under these circumstances and has as an object providing a holder of a test piece that is adapted to mount and fix the test piece on a fatigue tester by remote manipulation so that a fatigue test can be performed in either a hot vacuum or inert gas atmosphere.

This object of the present invention can be attained by a test piece holder that comprises a cylinder portion having a center hole through which a test piece is inserted, a reciprocating ram rod that is inserted into said hole from above and which is vertically slidable under hydraulic pressure to push down the test piece, and a test piece fixing plate that is inserted under the cylinder portion as it is slid horizontally from either right or left, with the thicker part of the test piece being compressively held between the fixing plate and the working end of the ram rod.

DETAILED DESCRIPTION OF THE INVENTION

Figure 1:
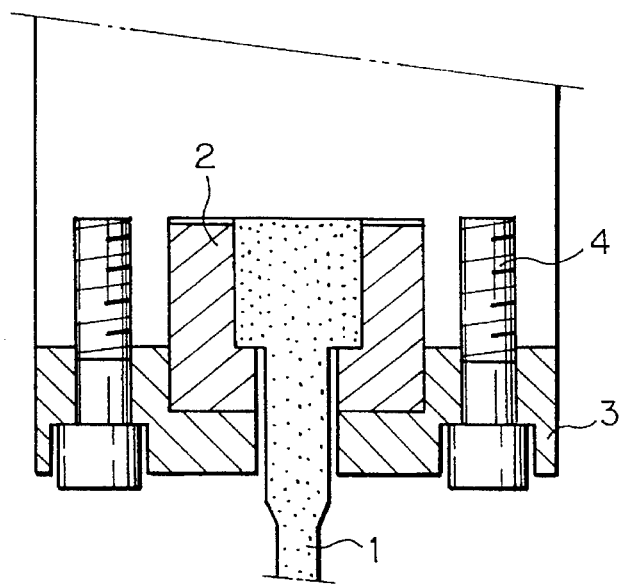
FIG. 1 is a sketch showing the construction of a conventional test piece holder which is to be operated manually.
Figure 2:
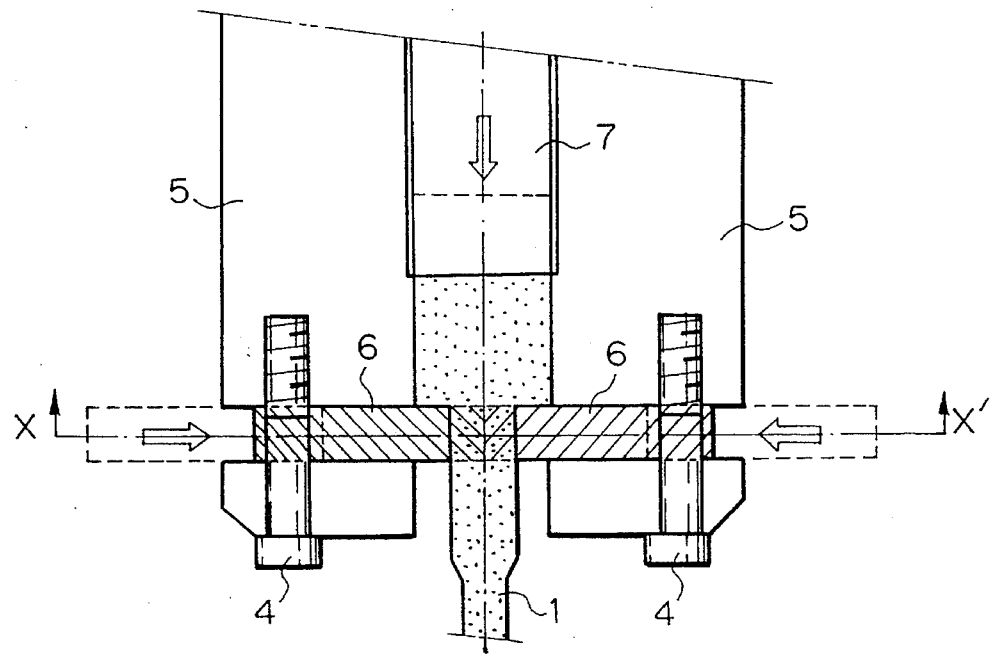
FIG. 2 is a sketch showing the construction of the test piece holder of the present invention which is to be operated under hydraulic pressure.

A sample holder according to an embodiment of the present invention is described below with reference to FIGS. 2 and 3.

The holder comprises a cylinder portion 5 having a center hole through which a fatigue test piece is inserted, a reciprocating ram rod 7 that is inserted into said hole from above and which is vertically slidable under hydraulic pressure to push down the test piece, and a test piece fixing plate 6 that is slidable horizontally under the cylinder portion from either right or left.

Figure 3:
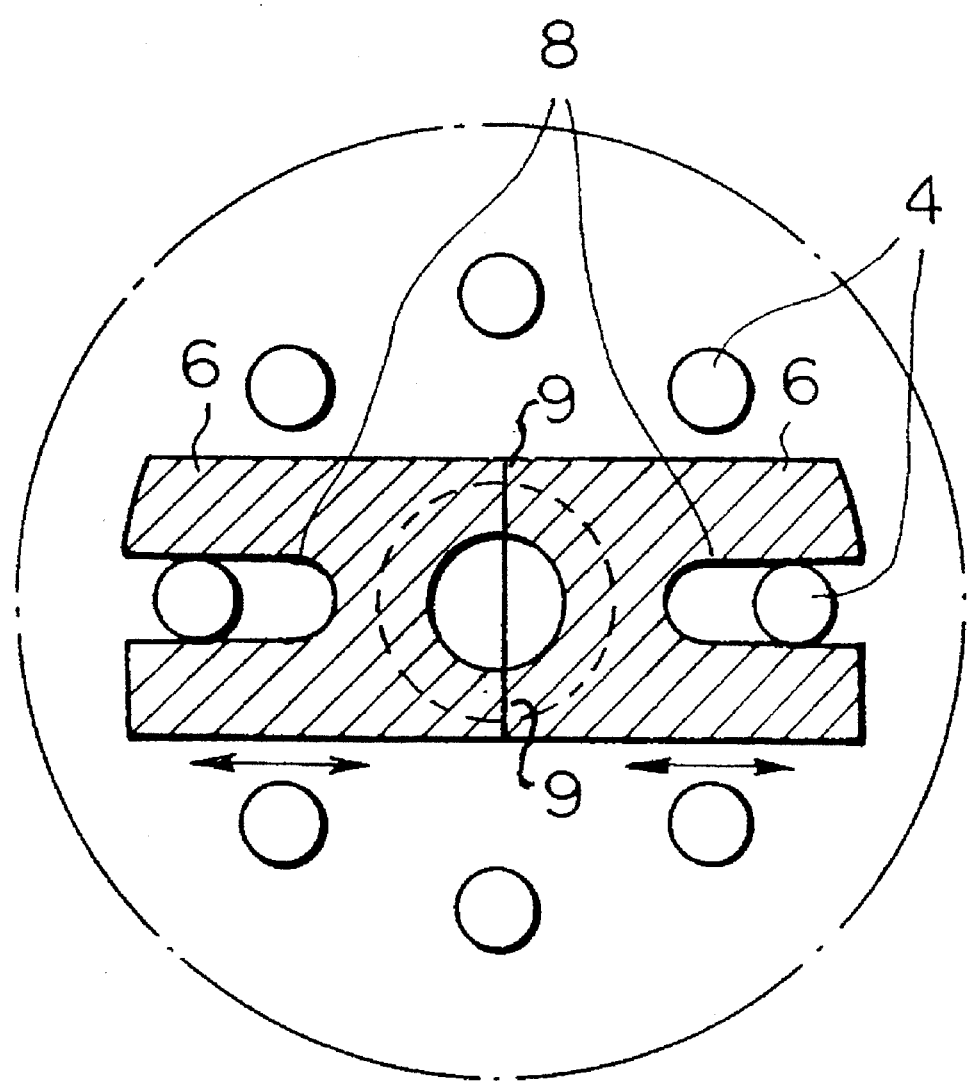
FIG. 3 is a cross section of the test piece holder of FIG. 2 as it is taken on line X—X'.

As shown more specifically in FIG. 3, the fixing plate 6 consists generally of two parts as divided along the center line 9, and it is of such a structure as to be slidable horizontally until it comes to a position where it can fix the test piece in the central portion. To this end, the fixing plate 6 has a groove 8 formed at both ends so that it can be slid horizontally as guided by fixing screws 4.

To operate the sample holder of the present invention, the upper thicker part of the fatigue test piece is first inserted into the center hole in the cylinder portion 5 from below. Then, the slidable fixing plate 6 is slid through a horizontal hole under the cylinder portion either from right or left towards the center of the cylinder portion until the thinner part of the test piece is gripped by the central opening in the fixing plate 6. Thus, the thinner part of the test piece is gripped by the fixing plate 6 so that it is fixed on the sample holder.

Thereafter, the reciprocating ram rod 7 as it is driven under hydraulic pressure is pushed into the center hole in the cylinder portion from above, whereby the top of the thicker part of the test piece is depressed under the working end of the ram rod 7 in such a way that the test piece is held in position between the descending rod 7 and the stationary fixing plate 6.

The holder of the present invention which is constructed in the manner described on the foregoing pages offers the advantage that tile insertion of the test piece into the center hole in the cylinder portion, the sliding of the fixing plate in a horizontal direction and the moving of the ram rod in a vertical direction can all be effected by remote manipulation, thus eliminating the need to perform direct, hands-on contact operation as in the prior art, such as threading the fixing screws through the fixing plate so that the test piece is fixed to the holder. As a result, the operator can be protected from any hazard that may be involved in the handling of certain test pieces.

If the test piece to be examined is a material that has been exposed to neutron radiation in a nuclear reactor and other radioactive environments, it is necessary to handle the radioactive test piece by remote manipulation so as to protect the worker from radiation. The sample holder of the present invention is equipped with the test piece pushing rod 7 which is operated vertically under hydraulic pressure and the test piece fixing plate 6 which is slidable horizontally, and part of the test piece is held between the descending rod 7 and the stationary plate 6. Because of this structural design, the holder enables the test piece to be fixed by remote manipulation and this eventually offers the advantage that a fatigue test can be performed on the sample without destroying the initially set hot vacuum or inert gas atmosphere.

What is claimed is:

1. A holder of a test piece on a fatigue tester that comprises a cylinder portion having a center hole through which the test piece is inserted, a reciprocating ram rod that is inserted into said hole from above and which is vertically slidable under hydraulic pressure to push down the test piece, and a test piece fixing plate that is inserted under said cylinder portion, said test piece fixing plate being slidable from either right or left at a lower end of said cylinder portion in a horizontal direction generally perpendicular to the direction of movement of said ram rod such that the thicker part of the test piece is compressively held between said fixing plate and the working end of said ram rod after said test piece is inserted into said center hole from below;

wherein said test piece fixing plate includes a first part and a second part, said first and second parts being horizontally slidable from opposing directions between an upper section and a lower section of said cylinder portion such that an upper generally planar surface of said fixing plate slides along a horizontal surface of said upper section of said cylinder portion and a lower generally planar surface of said fixing plate slides along a horizontal surface of said lower section;

wherein said upper section and said lower section of said cylinder portion are releasably joined together by at least two securing elements; and wherein said securing elements limit the horizontal sliding movement of said first and second parts of said fixing plate.

2. The holder of claim 1 wherein said first part and said second parts of said fixing plate each include a cut out region therein.

3. The holder of claim 1 wherein said first and second parts of said fixing plate join together to form a fixing plate center hole in the center thereof such that the test piece is gripped by said fixing plate fixing hole.

4. The holder of claim 1 wherein the test piece is fixed within said holder by remote manipulation external to said cylinder portion.

5. The holder of claim 1 wherein said reciprocating ram, said test piece fixing plate, and the test piece are capable of being remotely manipulated by a mechanism external to said cylinder portion.

6. The holder of claim 2 wherein each said securing element contacts one said cut out region of each said part of said fixing plate to limit the sliding movement thereof.

* * * * *